(12) United States Patent
Aubets Mir

(10) Patent No.: US 11,602,515 B2
(45) Date of Patent: Mar. 14, 2023

(54) PHARMACEUTICAL COMPOSITIONS COMPRISING DIMETHYL FUMARATE

(71) Applicant: Almirall, S.A., Barcelona (ES)

(72) Inventor: Jorge Aubets Mir, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 16/625,092

(22) PCT Filed: Jun. 25, 2018

(86) PCT No.: PCT/EP2018/066970
§ 371 (c)(1),
(2) Date: Dec. 20, 2019

(87) PCT Pub. No.: WO2018/234584
PCT Pub. Date: Dec. 27, 2018

(65) Prior Publication Data
US 2020/0197348 A1    Jun. 25, 2020

(30) Foreign Application Priority Data

Jun. 23, 2017   (GB) ...................................... 1710114
Jun. 27, 2017   (EP) ...................................... 17382402

(51) Int. Cl.
| | | |
|---|---|---|
| A61K 31/225 | (2006.01) |
| A61P 17/06 | (2006.01) |
| A61K 9/00 | (2006.01) |
| A61K 9/20 | (2006.01) |
| A61K 9/28 | (2006.01) |

(52) U.S. Cl.
CPC .......... *A61K 31/225* (2013.01); *A61K 9/0053* (2013.01); *A61K 9/2009* (2013.01); *A61K 9/2018* (2013.01); *A61K 9/2054* (2013.01); *A61K 9/2813* (2013.01); *A61K 9/2846* (2013.01); *A61P 17/06* (2018.01)

(58) Field of Classification Search
CPC .. A61K 31/225; A61K 9/0053; A61K 9/2009; A61K 9/2018; A61K 9/2054; A61K 9/2813; A61K 9/2846; A61P 17/06
See application file for complete search history.

(56) References Cited

U.S. PATENT DOCUMENTS

| | | |
|---|---|---|
| 6,509,376 B1 | 1/2003 | Joshi et al. |
| 2004/0054001 A1 | 3/2004 | Joshi et al. |
| 2008/0300217 A1 | 12/2008 | Nilsson |
| 2016/0310457 A1 | 10/2016 | Planells |
| 2021/0330628 A1 | 10/2021 | Almirall |

FOREIGN PATENT DOCUMENTS

| | | |
|---|---|---|
| EP | 2316430 B1 | 6/2012 |
| WO | 2006/037342 A2 | 4/2006 |
| WO | WO2006/116596 A2 | 11/2006 |
| WO | 2007/042034 A1 | 4/2007 |
| WO | WO2009/118764 A1 | 10/2009 |
| WO | 2010/079221 A1 | 7/2010 |
| WO | 2010/079222 A1 | 7/2010 |
| WO | WO2010/126605 A1 | 11/2010 |
| WO | WO2012/164060 A1 | 12/2012 |
| WO | WO2013/119677 A1 | 8/2013 |
| WO | 2015/086467 A1 | 6/2015 |
| WO | 2016081676 A1 | 5/2016 |

OTHER PUBLICATIONS

Nikolic et al., "Effect of Selected Direct Compression Excipients on the Stability of Acetylsalicylic Acid Tablets," Pharm. Ind. vol. 57, No. 11, pp. 958-963 (1995).
"Committee for Medicinal Products for Human Use (CHMP), Assessment Report Tecfidera," European Medicines Agency, Science Medicines Health, Nov. 26, 2013 (136 pages).
International Search Report and Written Opinion for International Application No. PCT/EP2014/076767, dated Feb. 20, 2015 (10 pages).
Office Action dated Sep. 16, 2016, during prosecution of U.S. Appl. No. 15/103,465 (9 pages).
Office Action dated Mar. 6, 2017, during prosecution of U.S. Appl. No. 15/103,465 (13 pages).
Office Action dated Sep. 13, 2017, during prosecution of U.S. Appl. No. 15/103,465 (12 pages).
Office Action dated Oct. 15, 2018, during prosecution of U.S. Appl. No. 15/103,465 (17 pages).
Office Action dated Apr. 22, 2019, during prosecution of U.S. Appl. No. 15/103,465 (18 pages).
FMC Health & Nutrition webpage (www.fmcbiopolymer.com/Pharmaceutical/Products/AcDiSol.aspx); downloaded Sep. 9, 2016. (2 pages).
Comments by Forward Pharma, Opposition proceedings for European Patent No. 2316430, filed Jun. 5, 2014 (43 pages).
Comparative Study by Forward Pharma, Opposition proceedings for European Patent No. 2316430, filed Jun. 5, 2014 (4 pages).
Declaration by Forward Pharma, Opposition proceedings for European Patent No. 2316430, filed Jun. 19, 2015 (4 pages).
Declaration by Synthon, Opposition proceedings for European Patent No. 2316430, filed Mar. 5, 2013 (4 pages).
English translation of FUMADERM® Package Insert, Jan. 2016 (10 pages).
FUMADERM® Package Insert, Jan. 2016 (German) (4 pages).
PCT Written Opinion prepared for International Application No. PCT/EP2018/066970, dated Sep. 13, 2018 (5 pages).
PCT International Search Report prepared for International Application No. PCT/EP2018/066970, dated Sep. 13, 2018 (3 pages).
Litjens et al., "Pharmacokinetics of oral fumarates in healthy subjects," British Journal of Clinical Pharmacology, vol. 58, No. 4, pp. 429-432 (2004).

(Continued)

*Primary Examiner* — Snigdha Maewall
(74) *Attorney, Agent, or Firm* — Sonapat LLC

(57) ABSTRACT

Pharmaceutical compositions are described comprising (a) dimethyl fumarate, (b) a diluent selected from monosaccharides, disaccharides, starch and starch derivatives, calcium and magnesium inorganic salts, sugar alcohols, and mixtures thereof, (c) microcrystalline cellulose and (d) croscarmellose sodium, wherein the dimethyl fumarate is not covered with a gastroresistant coating. These compositions are intended for the treatment of some inflammatory autoimmune diseases or disorders.

16 Claims, No Drawings

(56) References Cited

OTHER PUBLICATIONS

Office Action dated Nov. 13, 2020, during prosecution of U.S. Appl. No. 15/103,465 (21 pages).
Office Action dated Feb. 11, 2020, during prosecution of U.S. Appl. No. 15/103,465 (18 pages).
U.S. Appl. No. 17/316,861, filed May 11, 2021, of Applicant Alrmirall, S.A., and inventors Maria Planells Jimenez, Begoña Duarte Lopez and Pere Guiro Coll (35 pages).
Walker et al., "Fumaderm® in daily practice for psoriasis: dosing, efficacy and quality of life," British Journal of Dermatology, vol. 171, pp. 1197-1205 (2014).
Abstract of Milenkovic et al., "Beneficial effects of dimethyl fumarate on experimental autoimmune myocarditis," Arch Med Res. vol. 39, pp. 639-646 (2008) (2 pages).
Scuderi et al., "Antioxidant and Anti-inflammatory Effect of Nrf2 Inducer Dimethyl Fumarate in Neurodegenerative Diseases," Antioxidants, vol. 9, pp. 1-15 (2020).
Balak et al., "Treatment of lupus erythematosus with fumaic acid ester derivatives: two case-reports," J. Transl Med., vol. 9(Suppl 2), p. 15 (2011) (2 pages).
Casili et al., "Dimethyl Fumarate Reduces Inflammatory Responses in Experimental Colitis," Journal of Crohn's and Colitis, pp. 472-483 (2016).
Office Action dated Oct. 27, 2021, during prosecution of U.S. Appl. No. 17/316,861 (10 pages).
Office Action dated May 4, 2022, during prosecution of U.S. Appl. No. 17/316,861 (16 pages).
"Ethyl Cellulose," Prepared at the 26th JECFA (1982), published in FNP 25 (1982) and FNP 52 (1992), obtained from http://www.fao.org/fileadmin/user_upload/jecfa_additives/docs/Monograph1/additive-178-m1 .pdf on Dec. 19, 2019 (2 pages).
"Specifications and test methods for EUDRAGIT® RL 12,5 and EUDRAGIT® RL 100, EUDRAGIT® RS 12,5 and EUDRAGIT® RS 100," obtained from https://chemistry.mdma.ch/hiveboard/picproxie_docs/000494861-6_5_1_7.pdf on Dec. 19, 2019 (6 pages).
BASF, "Kollicoat® SR 30 D, The coating polymer for pH-independent sustained release formulations," obtained from https://pharmaceutical.basf.com/en/Drug-Formulation/Kollicoat-SR-30-D.html on Dec. 23, 2019 (5 pages).
Sonje et al., "Comprehensive Review on Eudagrit Polymers," Int. Res. J. Pharm., vol. 4, pp. 71-74 (2013).
Satish Singh Kadian et al., "Eudragit and its Pharmaceutical Significance," Roorkee College of Pharmacy (2009) (16 pages).
Mrowietz et al., "Efficacy and safety of LAS41008 (dimethyl fumarate) in adults with moderate-to-severe chronic plaque psoriasis: a randomized, double-blind, Fumaderm- and placebo-controlled trial (BRIDGE)," British Journal of Dermatology, vol. 176, pp. 615-623 (2017).
Cada et al., "Formulary Drug Reviews: Dimethyl Fumarate," Hosp Pharm, vol. 48, pp. 668-679 (2013).
Masaki Kitamura, "Relationship Between Diet and Drugs," Ziten (O.R.L Tokyo), vol. 45, No. 4, pp. 292-295 (36-39) (2002).
Partial English Translation of Masaki Kitamura, "Relationship Between Diet and Drugs," Ziten (O.R.L Tokyo), vol. 45, No. 4, pp. 292-295 (36-39) (2002) (1 page).

PHARMACEUTICAL COMPOSITIONS COMPRISING DIMETHYL FUMARATE

FIELD OF THE INVENTION

The present invention relates to a method of treating an inflammatory autoimmune disorder by administration of pharmaceutical compositions comprising (a) particles of dimethyl fumarate, (b) lactose, (c) microcrystalline cellulose and (d) croscarmellose sodium, wherein the particles of dimethyl fumarate are not covered with a gastro-resistant coating.

BACKGROUND OF THE INVENTION

Inflammatory or autoimmune diseases or disorders such as rheumatoid arthritis, multiple sclerosis (MS), amyotrophic lateral sclerosis, Crohn's disease, ulcerative colitis, systemic lupus erythematosus (SLE), myastenia gravis, acute disseminated encephalomyelitis, idiopathic thrombocytopenic purpura, Sjoegren's syndrome, autoimmune hemolytic anemia (AIHA), type I diabetes and psoriasis, are a major health burden especially in industrialized countries. These disorders in general cannot be cured, but the condition can be controlled or reduced in many cases.

Fumaric acid esters (FAE) are chemical compounds derived from unsaturated dicarboxylic fumaric acid and have been used in the treatment of psoriasis for years, originally proposed by the German chemist Walter Schweckendiek.

In 1994, Fumaderm® (Fumapharm AG), a mixture of dimethyl fumarate (DMF) and calcium, magnesium and zinc salts of monoethyl fumarate (MEF), was approved for the treatment of psoriasis in Germany. Fumaderm® is available in two different dosage strengths: low strength tablets (Fumaderm® initial) containing 30 mg dimethylfumarate, 67 mg Ca-ethylhydrogenfumarate, 5 mg Mg-ethylhydrogenfumarate and 3 mg Zn-ethylhydrogenfumarate; and high strength tablets (Fumaderm®) containing 120 mg dimethylfumarate, 87 mg Ca-ethylhydrogenfumarate, 5 mg Mg-ethylhydrogenfumarate and 3 mg Zn-ethylhydrogenfumarate.

Both Fumaderm® initial and Fumaderm® are enteric-coated tablets containing the following excipients: croscarmellose sodium, talc, magnesium stearate, coloring agent E171 and E132 (only in Fumaderm®), methacrylic acid-methylmethacrylate-copolymer (1:1), methacrylic acid-ethylacrylate-copolymer (1:1), Macrogol 6000, simethicone, povidone, triethyl citrate, microcrystalline cellulose, and highly disperse silicon dioxide. In addition, the tablets should be stored not above 25° C. (Fumaderm® initial/Fumaderm®; Summary of Product Characteristics, version February 2009).

FAE therapy is associated with adverse events such as gastrointestinal complaints, flushing or decreasing in lymphocyte counts. In order to improve safety and efficacy of Fumaderm®, guidelines for the treatment of severe psoriasis with FAE were established in 1999 (Mrowietz U. et al, British Journal of Dermatology 1999, 141, 424-429). The two dosage strengths of Fumaderm® are intended to be applied in an individually base dosage regime starting with Fumaderm® initial in an escalating dose, and after some weeks of treatment, e.g. three weeks, switching to Fumaderm®.

FAE therapy is often required on a medium or long term basis to treat conditions such as psoriasis. For that reason, a pharmacokinetic profile in which the active ingredient is released gradually over the time interval between repeat dosages can be advantageous. To this end, WO 2006/037342, WO 2007/042034, WO 2010/079221 and WO 2010/079222 describe controlled release pharmaceutical compositions comprising dimethylfumarate in which the individual dimethylfumarate particles are coated with a polymer. Coating of the individual dimethylfumarate particles allows controlled release of the active ingredient at a predetermined rate.

WO 2015/086467 discloses a pharmaceutical composition containing ingredients (a) to (d) set out above, but does not discuss the best way of administering that specific composition to a patient, to secure the most advantageous clinical outcome. The pharmacokinetics of a fumarate tablet containing dimethylfumarate and calcium-monoethylfumarate (i.e. which lacks the magnesium and zinc monoethylfumarate salts present in fumaderm) are discussed in Litjens et al, British Journal of Clinical Pharmacology, 2004, 58:4, 429. That document specifically advocates dosing of fumarate to patients before meals (i.e. in a fasted state).

SUMMARY OF THE INVENTION

It has now surprisingly been found that a new formulation of dimethyl fumarate has an advantageous pharmacokinetic profile. The present invention therefore provides a method of treating an inflammatory autoimmune disorder in a subject, which method comprises administering to the subject a therapeutically effective amount of a pharmaceutical composition comprising:

(a) particles of dimethyl fumarate;
(b) lactose;
(c) microcrystalline cellulose; and
(d) croscarmellose sodium, wherein the dimethyl fumarate particles are not covered with a gastro-resistant coating, and wherein the composition is administered to the subject during or within one hour after a meal.

It is a finding of the invention that the specific pharmaceutical composition detailed above has improved pharmacokinetic properties, as compared with known formulations of dimethyl fumarate such as Fumaderm, and also enables a reduction in adverse events, particularly when administered during or within one hour after a meal.

The pharmaceutical composition of the invention also enables improved storage stability. Thus, the storage conditions of the pharmaceutical composition of the invention are less restrictive than the conditions indicated in the prescribing information for Fumaderm® and Tecfidera®. Further, despite having reduced the number of active ingredients from Fumaderm® and having different excipients, the pharmaceutical composition of the invention presents a dissolution profile similar to Fumaderm®.

The inflammatory autoimmune disorder which can be treated with the composition of the invention is typically an inflammatory or autoimmune disease or disorder selected from rheumatoid arthritis, multiple sclerosis (MS), amyotrophic lateral sclerosis, Crohn's disease, ulcerative colitis, systemic lupus erythematosus (SLE), myastenia gravis, acute disseminated encephalomyelitis, idiopathic thrombocytopenic purpura, Sjoegren's syndrome, autoimmune hemolytic anemia (AIHA), type I diabetes or psoriasis. More preferably, it is multiple sclerosis or psoriasis. Most preferably, it is psoriasis.

DETAILED DESCRIPTION OF THE INVENTION

The term "treatment" as used herein refers to the treatment of a disease or medical condition in a human patient which includes:

(a) preventing the disease or medical condition from occurring, i.e., prophylactic treatment of a patient;
(b) ameliorating the disease or medical condition, i.e., causing regression of the disease or medical condition in a patient;
(c) suppressing the disease or medical condition, i.e., slowing the development of the disease or medical condition in a patient; or
(d) alleviating the symptoms of the disease or medical condition in a patient.

The term "therapeutically effective amount" of a compound or composition as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "not covered with a gastro-resistant coating" as used herein means that dimethyl fumarate particles are not coated with a pharmaceutical acceptable polymer, for example a polymer such as ethylcellulose, methacrylic/acrylic acid copolymers or ammonio methacrylate copolymers (such as ammonio methacrylate copolymer type A or B, or methacrylic acid copolymer A or B), polyvinyl acetate polymer, methacryl-ethylacetate polymer; or hydrophilic excipients such as polyethylene glycol (PEG), povidone, hydroxyl propyl cellulose (HPC), hydroxyethyl starch (HES) or hydroxypropyl methyl cellulose (HPMC).

As used herein, a "Fumaderm" formulation is a tablet which contains dimethylfumarate, calcium monoethylfumarate, magnesium monoethylhydrogenfumarate, zinc monoethylfumarate, and croscarmellose sodium, magnesium stearate, microcrystalline cellulose, and colloidal anhydrous silica. The tablet is coated with a enteric coating which contains talc and methacrylic acid-methyl methacylate copolymer (1:1). The enteric coating may also contain Macrogol 6000, simethicone, povidone, triethyl citrate, titanium dioxide and indigo carmine (E-132).

Dimethyl Fumarate

Dimethyl fumarate (Dimethyl (E)-butenedioate; CAS RN 624-49-7) is the methyl ester of fumaric acid, which presents the molecular formula $C_6H_8O_4$ and the molecular mass 144.13 g/mol and the following chemical formula

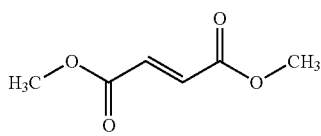

According to the German Medicines Codex 2004 (DAC 2004) it is a white crystalline powder having a melting point in the range from 102-105° C. The crystallographic properties of dimethyl fumarate are described Kooijman H et al, *Acta Cryst*. (2004), E60, o917-o918. Dimethyl fumarate can be obtained by reacting fumaric acid and methanol under the presence of concentrated sulphuric acid as catalyst (Ma Hongfei, *Chemical industry Times*, 2005, Vol. 19, No. 4, 18-19)

Typically, the dimethyl fumarate is sieved and/or milled to control its particle size. In a preferred embodiment the dimethyl fumarate has a particle size distribution d(10) between 5-20 µm, a d(50) between 30-70 µm, and a d(90) between 80-150 µm, measured using the laser diffraction particle size analyzer Mastersizer 2000 (Malvern Instruments).

Lactose Diluent

Diluents are fillers designated to make up the required bulk of the dosage form, i.e. tablet, when the drug dosage itself is inadequate to produce this bulk (*The Theory and Practice of Industrial Pharmacy*, 3rd edition, 1986, ISBN 0-8121-0977-5).

Lactose is a natural monosaccharide, obtained from milk, which consist of one galactose and one glucose moiety. Lactose occurs as white to off-white crystalline particles or powder. It is odourless and slightly sweet-tasty. *The Handbook of Pharmaceutical Excipients*, 6th edition, 2009, describes different lactose types which are suitable according to the current invention: anhydrous lactose (CAS RN 63-42-3; molecular formula $C_{12}H_{22}O_{11}$; molecular weight 342.30 g/m), inhalation lactose, lactose monohydrate (CAS RN 5989-81-1; molecular formula $C_{12}H_{22}O_{11}.H_2O$; molecular weight 360.31 g/m), and spray-dried lactose, which is a mixture of amorphous lactose (1:1 mixture of α-and-β-lactose) and lactose monohydrate.

In a preferred embodiment, the lactose is selected from lactose monohydrate or spray-dried lactose, preferably spray-dried lactose.

Typically, the spray-dried lactose has a bulk density between 0.55 and 0.68 g/cm³ and a tapped density between 0.65 and 0.75 g/cm³. In a preferred embodiment the spray-dried lactose has a particle size distribution (retained on air jet sieve, cumulative) 75 µm (US standard #200) 60-80%, 106 µm (US standard #140) 30-55% and 250 µm (US standard #60) 0.0-0.5%.

Microcrystalline Cellulose

Microcrystalline cellulose (CAS RN 9004-34-6; molecular formula $(C_6H_{10}O_5)_n$ where n is approx. 220; molecular weight approx. 36000 g/m) is a purified, partially depolymerized cellulose that occurs as a white, odourless, tasteless, crystalline powder composed of porous particles (*Handbook of Pharmaceutical Excipients*, 6th edition, 2009).

Typically, the microcrystalline cellulose has a bulk density between 0.28 and 0.33 g/cm³. In a preferred embodiment the microcrystalline cellulose has a particle size distribution d(10) between 25-50 µm, a d(50) between 100-150 µm, and a d(90) between 195-280 µm, measured using a laser diffraction particle size analyzer Mastersizer (Malvern Instruments).

Croscarmellose Sodium

Croscarmellose sodium (cellulose, carboxymethyl ether, sodium salt, crosslinked; CAS RN 74811-65-7) is a cross-linked polymer of carboxymethyl cellulose sodium. Croscarmellose sodium occurs as an odourless, white or grayish white powder (*Handbook of Pharmaceutical Excipients*, 6th edition, 2009).

Typically, the croscarmellose sodium has a bulk density around 0.529 g/cm³ and a tapped density between around 0.819 g/cm³. In a preferred embodiment the microcrystalline cellulose has a particle size distribution d(10) of not more than 25 µm, a d(50) between 25-55 µm, and a d(90) of not less than 60 µm, measured using a laser diffraction particle size analyzer Mastersizer (Malvern Instruments).

The Pharmaceutical Compositions

In a preferred embodiment, the pharmaceutical composition as defined above further comprises (e) at least one glidant.

Typically, the glidant (e) is selected from calcium phosphate, calcium silicate, powdered cellulose, magnesium silicate, magnesium trisilicate, magnesium carbonate, magnesium oxide, magnesium lauryl sulphate, sodium lauryl sulphate starch, silicon dioxide, talc, colloidal silica, colloidal anhydrous silica (colloidal silicon dioxide or fumed silicon dioxide) and mixtures thereof.

Preferably, the glidant (e) is selected from colloidal silica anhydrous, talc, or a combination thereof, more preferably colloidal anhydrous silica.

In a preferred embodiment, the pharmaceutical composition as defined above further comprises (f) at least one lubricant.

Typically, the lubricant (f) is selected from magnesium stearate, calcium stearate, sodium stearyl fumarate, polyethylene glycol (in particular polyethylene glycol 4000 and 6000), sodium lauryl sulfate, magnesium lauryl sulfate, sodium benzoate, potassium benzoate, light mineral oil, hydrogenated vegetable oils (in particular hydrogenated castor oil), glycerin monostearate, glyceryl behenate, glyceryl palmitostearate, stearic acid, zinc stearate, and mixtures thereof.

Preferably, the lubricant (f) is magnesium stearate.

Preferably, therefore, the pharmaceutical composition of the invention comprises (a) particles of dimethyl fumarate, (b) lactose, (c) microcrystalline cellulose, (d) croscarmellose sodium, (e) colloidal anhydrous silica and (f) magnesium stearate, wherein the particles of dimethyl fumarate are not covered with a gastro-resistant coating.

In a preferred embodiment, in the pharmaceutical composition as defined above the weight ratio (c) microcrystalline cellulose to (b) lactose diluent is in the range from 2:5 to 5:2, preferably in the range from 2:1 to 1:2, more preferably 4:3.

In another preferred embodiment, in the pharmaceutical composition as defined above the weight ratio (c) microcrystalline cellulose to (a) dimethyl fumarate is in the range from 5:1 to 1:5, preferably in the range from 3:1 to 1:3, more preferably 8:5.

In another preferred embodiment, in the pharmaceutical composition as defined above the weight ratio (b) lactose diluent to (c) dimethyl fumarate is in the range from 5:1 to 1:5, preferably in the range from 3:1 to 1:3, more preferably 6:5.

In another preferred embodiment, in the pharmaceutical composition as defined above the weight ratio (c) microcrystalline cellulose to (d) croscarmellose sodium is in the range from 30:1 to 1:5, preferably in the range from 20:1 to 1:2, more preferably 10:1.

In another preferred embodiment, in the pharmaceutical composition as defined above the weight ratio (b) lactose diluent to (d) croscarmellose sodium is in the range from 20:1 to 1:5, preferably in the range from 10:1 to 1:3, more preferably 15:2.

The pharmaceutical composition of the invention may optionally contain other conventional ingredients such as anti-oxidants, colorants, flavouring agents, preservatives and taste-masking agents.

In a preferred embodiment, the pharmaceutical composition of the invention is administered orally (peroral administration; per os (latin)).

Typically, the pharmaceutical composition of the invention is a solid dosage form, i.e. immediate-release tablet, immediate-release capsule, delayed-release tablet, delayed-release capsule, sustained-release tablet, sustained-release capsule, soluble tablet, dispersible tablet, effervescent tablet, chewable tablet, chewable gum, buccal tablet, sublingual tablet, orally disintegrating tablet, lozenge, pastille, hard gelatin capsule or soft gelatin capsule.

Preferably, the pharmaceutical composition of the invention is in the form of a delayed-release tablets, more preferably a gastro-resistant (enteric coated) tablet. Gastro-resistant tablets are delayed-release tablets that are intended to resist the gastric fluid and to release their active substance(s) in the intestinal media. Usually they are prepared from granules or particles already covered with a gastro-resistant coating or in certain cases by covering tablet cores with a gastro-resistant coating (enteric coated tablets) (*European Pharmacopoeia* 6.0, 2007, ISBN 9789287160546). In a preferred embodiment, the pharmaceutical composition of the invention is in the form of a gastro-resistant (enteric coated) tablet prepared by covering tablet cores with a gastro-resistant coating.

As previously indicated, the dimethyl fumarate particles are not covered with a gastro-resistant coating. However, the tablet containing components (a) to (d) set out above may be covered with such a coating.

Tablet blends may be compressed directly or by roller to form tablets. Tablet blends or portions of blends may alternatively be wet-, dry-, or melt-granulated, melt congealed, or extruded before tableting. The formulation of tablets is discussed in detail in *Remington: The Science and Practice of Pharmacy,* 21st Edition, 2005, ISBN 0781746736.

Coatings on tablet cores usually consist of a mixture of substances, for example, one or more plasticizers, one or core polymers, one or more copolymers, one or more glidants, one or more pigments, or mixtures thereof. Coating of tablet cores is discussed in detail in *Pharmaceutical Manufacturing Handbook: Production and Processes,* 2008, ISBN 9780470259580.

Examples of suitable plasticizers in the coating (compounds which reduce the minimum film-forming temperatures as well as the glass transition temperature) include one or more of acetyltributyl citrate, acetyltriethyl citrate, benzyl benzoate, cellulose acetate phthalate, chlorbutanol, dextrin, dibutyl phthalate, dibutyl secacate, diethyl phthalate, dimethyl phthalate, glycerin, glycerin monostearate, hypromellose phthalate, mannitol, mineral oil, lanolin alcohol, palmitic acid, polyethylene glycol, polyvinyl acetate phthalate, propylene glycol, 2-pyrrolidone, sorbitol, stearic acid, triacetin, tributyl citrate, triethanolamine, triethyl citrate, dibutyl sebacate, polyethylene glycol and propylene glycol.

Examples of suitable polymers in the coating include one or more of methacrylic acid polymers, acrylic polymers, hydroxypropyl methylcellulose (HPMC), hydroxypropyl cellulose acetate succinate (HPMCAS), ethylcellulose (EC), carboxymethyl ethylcellulose (CMEC), poly(vinyl alcohol) (PVA), and polyvinyl acetate phthalate (PVAP). These polymers are available as aqueous dispersions, powders or organic solutions (e.g. alcohols, acetone). An example of commercially available organic solution is a mixture of poly(vinyl alcohol), methacrylic acid copolymer-type C, polyethylene glycol, talc, a neutralizing agent and pigment; marketed under the trade name OPADRY® 200 by Colorcon, Inc.

Examples of suitable copolymers in the coating include one or more of methacrylic acid-methyl methacrylate (50:50) copolymer, methacrylic acid-methyl methacrylate (30:70) copolymer, methacrylic acid-ethylacrylate (50:50) copolymer, or a methacrylic acid-methyl acrylate-methyl methacrylate copolymer. These copolymers are available as aqueous dispersions, powders or organic solutions (e.g. alcohols, acetone). Examples of commercially available copolymers include the methacrylic acid copolymers marketed under the trade name EUDRAGIT® by Evonik, which include EUDRAGIT® L 30 D-55 (methacrylic acid-ethyl acrylate copolymer (1:1), 30% aqueous dispersion), EUDRAGIT® L 100-55 (methacrylic acid-ethyl acrylate copolymer (1:1), powder form), EUDRAGIT® L 100 (methacrylic acid-methyl methacrylate copolymer (1:1), powder form), EUDRAGIT® L 12,5 (methacrylic acid-methyl methacrylate copolymer (1:1), 12.5% organic solution), EUDRAGIT® S 100 (methacrylic acid-methyl methacrylate copolymer (1:2), powder form), EUDRAGIT® S 12,5 (methacrylic acid-methyl methacrylate copolymer (1:1), 12.5% organic solution) and EUDRAGIT® FS 30 D (methacrylic acid-methyl acrylate-methyl methacrylate copolymer, 30% aqueous dispersion).

Examples of suitable glidants in the coating include talc or glycerol monostearate.

Examples of suitable pigments in the coating include titanium dioxide, aluminium lakes, indigo carmine lakes or iron oxide pigments.

In a particular embodiment, the pharmaceutical composition of the invention is a tablet which is coated with a coating formulation which comprises i) one or more polymers and/or copolymers, ii) one or more glidants, iii) one or more plasticizers, and iv) one or more pigments. Optionally, the coating formulation can comprise one or more antifoam agents.

Preferably, the coating comprises talc and a methacrylic acid-ethyl acrylate copolymer. More preferably, the coating further comprises simethicone, triethyl citrate, titanium dioxide, indigo carmine and sodium hydroxide.

In a preferred embodiment, the composition of the invention comprises:
(a) particles of dimethyl fumarate, in an amount of 1 part by weight,
(b) lactose, in an amount of from 0.9 to 1.3 parts by weight;
(c) microcrystalline cellulose, in an amount of from 0.1 to 0.2 parts by weight;
(d) croscarmellose sodium, in an amount of from 0.1 to 0.2 parts by weight;
(e) optionally, colloidal anhydrous silica in an amount of from 0.01 to 0.03 parts by weight; and
(f) optionally, magnesium stearate in an amount of from 0.01 to 0.03 parts by weight,
wherein the particles of dimethyl fumarate are not covered with a gastro-resistant coating.

In a further preferred embodiment, the pharmaceutical composition of the invention is in the form of a gastro-resistant (enteric coated) tablet and comprises, based on the total weight of the tablet previous to coating (tablet core):
(a) 20-30 wt. % of dimethyl fumarate (not previously covered with a gastro-resistant coating);
(b) 25-35 wt. % of a lactose diluent;
(c) 35-45 wt. % of microcrystalline cellulose;
(d) 1-10 wt. % of croscarmellose sodium.

When the gastro-resistant (enteric coated) tablet as defined above comprises (e) at least one glidant, the glidant (or combination of glidants) is present in an amount ranging from 0.1 to 5 wt. %, preferably from 0.2 to 3 wt. %, more preferably from 0.1 to 1 wt. %, based on the total weight of the tablet previous to coating (tablet core).

When the gastro-resistant (enteric coated) tablet as defined above comprises (f) at least one lubricant, the lubricant (or combination of lubricants) is present in an amount ranging from 0.1 to 10 wt. %, preferably from 0.2 to 5 wt. %, more preferably from 0.1 to 2 wt. %, based on the total weight of the tablet previous to coating (tablet core).

In a particular preferred embodiment, the pharmaceutical composition of the invention is in the form of a gastro-resistant (enteric coated) tablet and comprises, based on the total weight of the tablet previous to coating (tablet core):
(a) 20-30 wt. % of particles dimethyl fumarate (not covered with a gastro-resistant coating);
(b) 25-35 wt. % of lactose;
(c) 35-45 wt. % of microcrystalline cellulose;
(d) 1-10 wt. % of croscarmellose sodium;
(e) 0.1-5 wt. % of at least one glidant; preferably selected from colloidal anhydrous silica, talc, or a combination thereof; more preferably colloidal silica anhydrous;
(f) 0.1-10 wt. % of at least one lubricant, preferably magnesium stearate.

In a preferred embodiment, the pharmaceutical composition of the invention is in the form of a gastro-resistant (enteric coated) tablet and comprises, based on the total weight of the tablet previous to coating (tablet core):
(a) 25 wt. % of particles of dimethyl fumarate (not covered with a gastro-resistant coating);
(b) 30 wt. % of lactose;
(c) 40 wt. % of microcrystalline cellulose;
(d) 4 wt. % of croscarmellose sodium;
(e) 0.5 wt. % of at least one glidant; preferably selected from colloidal anhydrous silica, talc, or a combination thereof; more preferably colloidal silica anhydrous;
(f) 0.5 wt. % of at least one lubricant, preferably magnesium stearate.

In a particular preferred embodiment, the pharmaceutical composition of the invention is in the form of a gastro-resistant (enteric coated) tablet and comprises, based on the total weight of the tablet previous to coating (tablet core):
(a) 30 mg of particles of dimethyl fumarate (not covered with a gastro-resistant coating);
(b) 36 mg of lactose;
(c) 48 mg of microcrystalline cellulose;
(d) 4.8 mg of croscarmellose sodium;
(e) 0.6 mg of colloidal anhydrous silica;
(f) 0.6 mg of magnesium stearate.

In another particular preferred embodiment, the pharmaceutical composition of the invention is in the form of a gastro-resistant (enteric coated) tablet and comprises, based on the total weight of the tablet previous to coating (tablet core):
(a) 120 mg of particles of dimethyl fumarate (not previously covered with a gastro-resistant coating);
(b) 144 mg of lactose;
(c) 192 mg of microcrystalline cellulose;
(d) 19.2 mg of croscarmellose sodium;
(e) 2.4 mg of colloidal anhydrous silica;
(f) 2.4 mg of magnesium stearate.

In a preferred embodiment, when the pharmaceutical composition of the invention is in the form of a gastro-resistant (enteric coated) tablet, the tablet core does not contain further excipients than those described above, i.e. (b) lactose diluent, (c) microcrystalline cellulose, (d) croscarmellose sodium and optionally (e) colloidal anhydrous silica; and (f) magnesium stearate.

Typically, the pharmaceutical composition of the present invention contains less than 20 wt % of monoethylfumarate salts. More preferably, it contains less than 10 wt %, more preferably less than 5 wt %, more preferably less than 1 wt % of monoethylfumarate salts. Most preferably, it is substantially free of monoethylfumarate salts.

Method of Treating the Inflammatory Disorder

Typically, the pharmaceutical composition is administered to the subject during or within 30 minutes of a meal. Preferably, it is administered to the subject during or immediately after a meal. Thus, the subject is typically in a fed state when the pharmaceutical composition is administered.

Preferably, the subject is a mammal, more preferably a human.

Following administration of dimethyl fumarate to a subject, the active ingredient is rapidly hydrolysed in-vivo to the metabolite monomethyl fumarate. Typically, the plasma concentrations of monomethyl fumarate in the subject following administration of the pharmaceutical composition of the invention are such that the AUC(0-t) is from 10 to 19, preferably 12.5 to 16.5, ng·h/mL per mg of the dimethyl fumarate in the pharmaceutical composition. More preferably, the AUC(0-t) is from 13 to 15 ng·h/mL per mg of the dimethyl fumarate in the pharmaceutical composition. Typically, in this embodiment, the pharmaceutical composition comprises 30 or 120 mg dimethyl fumarate and is administered orally.

In a further embodiment of the invention, the plasma concentrations of monomethyl fumarate in the subject following administration of the pharmaceutical composition of the invention are such that the Cmax is less than 120%, preferably less than 110%, of that achievable by administration of a corresponding Fumaderm formulation having the same amount of dimethylfumarate, and the AUC(0-t) is greater than 130%, preferably greater than 150%, of that achievable by administration of a corresponding Fumaderm formulation having the same amount of dimethylfumarate.

The present invention also provides a method of treating an inflammatory autoimmune disorder in a subject, which method comprises administering to the subject a therapeutically effective amount of a pharmaceutical composition comprising:
 (a) particles of dimethyl fumarate;
 (b) lactose;
 (c) microcrystalline cellulose; and
 (d) croscarmellose sodium,
wherein the dimethyl fumarate is not covered with a gastro-resistant coating, and wherein the plasma concentrations of monomethyl fumarate in the subject following administration of the pharmaceutical composition are such that the AUC(0-t) is from 10 to 19, preferably 12.5 to 16.5, more preferably 13 to 15, ng·h/mL per mg of the dimethyl fumarate in the pharmaceutical composition.

Also provided is a method of treating an inflammatory autoimmune disorder in a subject, which method comprises administering to the subject a therapeutically effective amount of a pharmaceutical composition comprising:
 (a) particles of dimethyl fumarate;
 (b) lactose;
 (c) microcrystalline cellulose; and
 (d) croscarmellose sodium,
wherein the dimethyl fumarate is not covered with a gastro-resistant coating, and wherein the plasma concentrations of monomethyl fumarate in the subject following administration of the pharmaceutical composition are such that the Cmax is less than 120%, preferably less than 110%, of that achievable by administration of a corresponding Fumaderm formulation having the same amount of dimethylfumarate, and the AUC(0-t) is greater than 130%, preferably greater than 150%, of that achievable by administration of a corresponding Fumaderm formulation having the same amount of dimethylfumarate, In this embodiment, the pharmaceutical composition is typically administered orally, and the Cmax and AUC(0-t) achievable by administration of the Fumaderm formulation are achieved following oral administration of the Fumaderm formulation. The Fumaderm formulation used as a comparator is a tablet which contains dimethylfumarate, calcium monoethylfumarate, magnesium monoethylhydrogenfumarate, zinc monoethylfumarate, and croscarmellose sodium, magnesium stearate, microcrystalline cellulose, and colloidal anhydrous silica, and which is coated with a enteric coating which contains talc and methacrylic acid-methyl methacylate copolymer (1:1). The enteric coating may also contain Macrogol 6000, simethicone, povidone, triethyl citrate, titanium dioxide and indigo carmine (E-132).

Methods of Preparing the Pharmaceutical Composition

The pharmaceutical composition of the invention can be prepared by a process comprising the steps of:
 i) mixing (a) dimethyl fumarate, wherein the dimethyl fumarate is not previously covered with a gastro-resistant coating, (b) a lactose diluent, (c) microcrystalline cellulose, (d) croscarmellose sodium, and optionally other pharmaceutical excipients, to form a homogenous blend; and
 ii) optionally sieving the blend.

Preferred compositions of the invention can be prepared by a process comprising the steps of:
 i) mixing (a) dimethyl fumarate, wherein the dimethyl fumarate is not previously covered with a gastro-resistant coating, (b) a lactose diluent, (c) microcrystalline cellulose, (d) croscarmellose sodium, and (e) at least one glidant to form a homogenous blend;
 ii) optionally sieving the blend;
 iii) adding (e) at least one glidant to the previous blend and mixing the resulting blend; and
 iv) optionally sieving the final blend.

Gastro-resistant (enteric-coated) tablets as described above can be prepared by a process comprising the steps of:
 i) tableting the blend described above to obtain tablet cores; and
 ii) coating the tablet cores.

Combination Therapies

Typically, in the processes of the present invention, the pharmaceutical composition is administered in combination with a therapeutically effective amount of a compound that reduces or eliminates flushing.

Flushing is known as a side effect of fumaric acid esters since early clinical studies and has led to the discontinuation of treatment in some patients (Nieboer C et al., *Journal of the American Academy of Dermatology*, 1989, 20:4, 601-608); Nieboer C et al., *Dermatologica*, 1990, 181:33-37). Thus, "a compound that reduces or eliminates flushing" refers to the ability of a compound to reduce the severity of flushing when it occurs, or result in fewer flushing events than would otherwise occur. As used herein the term "therapeutically effective amount" means an amount sufficient to reduce the severity of flushing when it occurs, or result in fewer flushing events than would otherwise occur. An amount adequate to accomplish this is defined as a "therapeutically effective amount".

The compound that reduces or eliminates flushing can be present within the pharmaceutical composition of the invention, or it may be administered in a different pharmaceutical composition. In this latter scenario, the two compositions can be for separate, simultaneous, concomitant or sequential administration by the same or a different route.

Typically, the compound that reduces or eliminates flushing is selected from acetylsalicylic acid, laropripant ((−)-[(3R)-4-(4-chlorobenzyl)-7-fluoro-5-(methylsulfonyl)-1,2,3,4-tetrahydrocyclopenta[b]indol-3-yl]acetic acid), COX inhibitors, or a combination thereof.

As used herein, the term COX inhibitor refers to a compound that inhibits both the cyclooxygenase-1 enzyme and the cyclooxygenase-2 enzyme. In one embodiment, the compound has a cyclooxygenase-1 $IC_{50}$ value of less than about 200 μM, preferably of less than about 100 μM, more preferably of less than about 50 μM, even more preferably of less than about 20 μM, and a cyclooxygenase-2 $IC_{50}$ value of less than about 50 μM, preferably of less than 25 μM, more preferably of less than about 15 μM, even more preferably of less than about 2 μM, in the human whole blood assay (as described in Brideau et al., Inflamm Res., 45: 68-74 (1996)) and also has a selectivity ratio of cyclooxygenase-2 inhibition over cyclooxygenase-1 inhibition (determined as the ratio $IC_{50}$ COX-1/$IC_{50}$ COX-2) of at least 0.1, preferably of at least 0.5, more preferably of at least 1, even more preferably of at least 2, and most preferably of at least 10.

In an embodiment, the COX inhibitor is selected from the group consisting of oxicams, piroxicam, meloxicam, isoxicam, tenoxicam, sudoxicam, CP-14,304, salicylates, disalcid, benorylate, trilisate, safapryn, solprin, diflunisal, fendosal, acetic acid derivatives, aceclofenac, diclofenac, fenclofenac, indomethacin, sulindac, tolmetin, isoxepac, furofenac, tiopinac, zidometacin, acematacin, fentiazac, zomepirac, clindanac, oxepinac, felbinac, etodolac, ketorolac, fenamates, mefenamic, meclofenamic, flufenamic, niflumic, tolfenamic acids, propionic acid derivatives, acetaminophen (paracetamol), ibuprofen, naproxen, benoxaprofen, flurbiprofen, ketoprofen, piketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone, apricoxib, celecoxib, cimicoxib, deracoxib, etoricoxib, lumiracoxib, parecoxib sodium, rofecoxib, selenocoxib-1, valdecoxib, 2-(3,4-difluoro-phenyl)-4-(3-hydroxy-3-methyl-butoxy)-5-(4-methanesulfonyl-phenyl)-2H-pyridazin-3-one (ABT-963), 4-(4-Cyclohexyl-2-methyloxazol-5-yl)-2-fluorobenzenesulfonamide (JTE-522), N-[2-Cyclohexyloxy-4-nitrophenyl]methanesulfonamide (NS 398), (E)-(5)-(3,5-Di-tert-butyl-4-hydroxybenzylidene)-2-ethyl-1,2-isothiazolidine-1,1-dioxide (S-2474), 5(R)-thiosulfonamide-3(2H)-benzofuranone (SVT-2016), N-[7-[(methanesulfonyl)amino]-4-oxo-6-phenoxy-4H-1-benzopyran-3-yl] formamide (T-614), BMS-347070 (Bristol Myers Squibb), GSK-644784 (GlaxoSmithKline), RS 57067 (Roche Bioscience), SC-75416 (Pfizer), SC-58125 (Pfizer), SD-8381, 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, 3-(2,4-difluorophenoxy)-6-methyl-2-(4-(methylsulfonyl)phenyl)-4H-pyran-4-one, 3-(4-chlorophenoxy)-6-methyl-2-(4-(methylsulfonyl)phenyl)-4H-pyran-4-one, 3-(4-bromo-2-fluorophenoxy)-6-methyl-2-(4-(methylsulfonyl)phenyl)-4H-pyran-4-one, 3-(4-chloro-2-fluorophenoxy)-6-methyl-2-(4-(methylsulfonyl)phenyl)-4H-pyran-4-one, 3-(2,4-difluorophenoxy)-6-methyl-2-(4-(methylsulfinyl)phenyl)-4H-pyran-4-one, 3-(4-chloro-2-fluorophenoxy)-6-methyl-2-(4-(methylsulfinyl)phenyl)-4H-pyran-4-one, (S)-3-(2,4-difluorophenoxy)-6-methyl-2-(4-(methylsulfinyl)phenyl)-4H-pyran-4-one, (S)-3-(4-bromo-2-fluorophenoxy)-6-methyl-2-(4-(methylsulfinyl)phenyl)-4H-pyran-4-one, (S)-3-(4-chloro-2-fluorophenoxy)-6-methyl-2-(4-(methylsulfinyl)phenyl)-4H-pyran-4-one, (R)-3-(2,4-difluorophenoxy)-6-methyl-2-(4-(methylsulfinyl)phenyl)-4H-pyran-4-one, (R)-3-(4-bromo-2-fluorophenoxy)-6-methyl-2-(4-(methylsulfinyl)phenyl)-4H-pyran-4-one, (R)-3-(4-chloro-2-fluorophenoxy)-6-methyl-2-(4-(methylsulfinyl)phenyl)-4H-pyran-4-one, 4-(3-(2-fluorophenyl)-2-oxo-2,3-dihydrooxazol-4-yl)benzenesulfonamide, 4-(2-oxo-3-m-tolyl-2,3-dihydrooxazol-4-yl)benzenesulfonamide, 4-(2-oxo-3-p-tolyl-2,3-dihydrooxazol-4-yl)benzenesulfonamide, (R)-4-(4-(methylsulfinyl)phenyl)-3-phenylfuran-2(5H)-one, (S)-4-(4-(methylsulfinyl)phenyl)-3-phenylfuran-2(5H)-one, 4-(4-(methylsulfinyl)phenyl)-3-phenylfuran-2(5H)-one, 5-chloro-6'-methyl-3-(4-(methylsulfinyl)phenyl)-2,3'-bipyridine, (S)-5-chloro-6'-methyl-3-(4-(methylsulfinyl)phenyl)-2,3'-bipyridine, (R)-5-chloro-6'-methyl-3-(4-(methylsulfinyl)phenyl)-2,3'-bipyridine, and their pharmaceutically acceptable salts, their solvates, their N-oxides, their stereoisomers or their deuterated derivates thereof.

In a preferred embodiment, the COX inhibitor is selected from the group consisting of aceclofenac, diclofenac, acetaminophen (paracetamol), ibuprofen, naproxen, apricoxib, celecoxib, cimicoxib, deracoxib, etoricoxib, lumiracoxib, parecoxib sodium, rofecoxib, selenocoxib-1, valdecoxib, 2-(3,4-difluoro-phenyl)-4-(3-hydroxy-3-methyl-butoxy)-5-(4-methanesulfonyl-phenyl)-2H-pyridazin-3-one (ABT-963), 4-(4-Cyclohexyl-2-methyloxazol-5-yl)-2-fluorobenzenesulfonamide (JTE-522), N-[2-Cyclohexyloxy-4-nitrophenyl]methanesulfonamide (NS 398), (E)-(5)-(3,5-Di-tert-butyl-4-hydroxybenzylidene)-2-ethyl-1,2-isothiazolidine-1,1-dioxide (S-2474), 5(R)-thiosulfonamide-3(2H)-benzofuranone (SVT-2016), N-[7-[(methanesulfonyl)amino]-4-oxo-6-phenoxy-4H-1-benzopyran-3-yl] formamide (T-614), 3-(2,4-difluorophenoxy)-6-methyl-2-(4-(methylsulfonyl)phenyl)-4H-pyran-4-one, 4-(3-(2-fluorophenyl)-2-oxo-2,3-dihydrooxazol-4-yl)benzenesulfonamide, 4-(2-oxo-3-m-tolyl-2,3-dihydrooxazol-4-yl)benzenesulfonamide, 4-(2-oxo-3-p-tolyl-2,3-dihydrooxazol-4-yl)benzenesulfonamide, and their pharmaceutically acceptable salts, their solvates, their N-oxides, their stereoisomers or their deuterated derivates thereof.

In a further preferred embodiment, the COX inhibitor is selected from the group consisting of aceclofenac, diclofenac, acetaminophen (paracetamol), ibuprofen, naproxen, apricoxib, celecoxib, cimicoxib, deracoxib, etoricoxib, lumiracoxib, parecoxib sodium, rofecoxib, selenocoxib-1, valdecoxib, 3-(2,4-difluorophenoxy)-6-methyl-2-(4-(methylsulfonyl)phenyl)-4H-pyran-4-one, 4-(3-(2-fluorophenyl)-2-oxo-2,3-dihydrooxazol-4-yl)benzenesulfonamide, 4-(2-oxo-3-m-tolyl-2,3-dihydrooxazol-4-yl)benzenesulfonamide, 4-(2-oxo-3-p-tolyl-2,3-dihydrooxazol-4-yl)benzenesulfonamide, and their pharmaceutically acceptable salts, their solvates, their N-oxides, their stereoisomers or their deuterated derivates thereof.

Typically, in the processes of the present invention, the pharmaceutical composition is administered in combination with a therapeutically effective amount of a proton pump inhibitor (PPI). Proton pump inhibitors are a group of drugs whose main action is a pronounced and long-lasting reduction of gastric acid production and, therefore, reduce the gastrointestinal distress.

Typically, the proton pump inhibitor (PPI) is selected from dexlansoprazole, esomeprazole, ilaprazole, lansoprazole, omeprazole, pantoprazole, rabeprazole or mixtures thereof.

In a preferred embodiment, the proton pump inhibitor (PPI) is selected from lansoprazole, omeprazole, pantoprazole or mixtures thereof.

The active compounds in the combination may be administered together in the same pharmaceutical composition or in different compositions intended for separate, simultaneous, concomitant or sequential administration by the same or a different route.

In the processes of the present invention, the pharmaceutical composition of the invention may be administered with both a therapeutically effective amount of a compound that reduces or eliminates flushing as defined above and a therapeutically effective amount of a proton pump inhibitor (PPI) as defined above.

The present invention also provide a pharmaceutical comprising:
(a) particles of dimethyl fumarate;
(b) lactose;
(c) microcrystalline cellulose; and
(d) croscarmellose sodium,
wherein the dimethyl fumarate is not covered with a gastro-resistant coating, for use in any method of treating the human or animal body described above.

Also provided is the use of:
(a) particles of dimethyl fumarate;
(b) lactose;
(c) microcrystalline cellulose; and
(d) croscarmellose sodium,
wherein the dimethyl fumarate is not covered with a gastro-resistant coating, in the manufacture of a pharmaceutical composition as described in any embodiment set out above, which composition is for use in any method of treating the human or animal body described above.

The present invention also provides embodiments (1) to (22) set out below:

(1) A method of treating an inflammatory autoimmune disorder in a subject, which method comprises administering to the subject an oral pharmaceutical composition comprising dimethyl fumarate as the only fumaric acid derivative, wherein the plasma concentrations of monomethyl fumarate in the subject following administration of the pharmaceutical composition are such that the Cmax is from 8.3 to 14.2 ng/mL per mg of the dimethyl fumarate in the pharmaceutical composition and/or the AUC (0-t) is from 11 to 18 ng·h/mL per mg of the dimethyl fumarate in the pharmaceutical composition.
(2) A method according to (1) wherein the oral pharmaceutical composition comprises 30, 120 or 240 mg of dimethyl fumarate as the only fumaric acid derivative.
(3) A method according to (1) or (2), wherein the Cmax is from 8.3 to 11.5, or from 8.3 to 12, or from 8.3 to 12.5, or from 8.3 to 13, or from 8.3 to 13.5, or from 9 to 14.2, or from 9.5 to 14.2, or from 10 to 14.2, or from 10.5 to 14.2, or from 9 to 13.5, or from 9.5 to 13, or from 10 to 12.5, or from 10.5 to 12 ng/mL per mg of the dimethyl fumarate in the pharmaceutical composition
(4) A method according to any one of (1) to (3), wherein AUC (0-t) is from 11 to 15, or from 11 to 15.5, or from 11 to 16, or from 11 to 16.5, or from 11 to 17 or from 11 to 17.5, or from 11.5 to 18 or from 12 to 18, or from 12.5 to 18, or from 13 to 18 or from 13.5 to 18, or from 14 to 18, or from 11.5 to 17.5, or from 12 to 17, or from 12.5 to 16.5, or from 13 to 16, or from 13.5 to 15.5 or from 14 to 15 ng·h/mL per mg of the dimethyl fumarate in the pharmaceutical composition.
(5) A method according to any one of (1) to (4), wherein the oral pharmaceutical composition is in the form of a solid dosage form, more preferably in the form of a tablet or capsule, most preferably in the form of a tablet
(6) A method according to any of (1) to (5), wherein the oral pharmaceutical composition is an immediate, or sustained, or delayed release composition, most preferably an immediate release composition.
(7) A method according to any one of (1) to (6), wherein the pharmaceutical composition is administered during or immediately or within one hour after a meal.
(8) A method according to any one of (1) to (7), wherein the inflammatory or autoimmune disease or disorder is selected from rheumatoid arthritis, multiple sclerosis (MS), amyotrophic lateral sclerosis, Crohn's disease, ulcerative colitis, systemic lupus erythematosus (SLE), myasthenia gravis, acute disseminated encephalomyelitis, idiopathic thrombocytopenic purpura, Sjoegren's syndrome, autoimmune hemolytic anemia (AIHA), type I diabetes or psoriasis, most preferably psoriasis.
(9) A method according to any one of (1) to (8), wherein the plasma concentrations of monomethyl fumarate in the subject following administration of the pharmaceutical composition in the fed state are such that the Cmax is not less than 85%, preferably not less than 90% of the Cmax achievable following administration in a fasted state.
(10) A method according to any one of (1) to (9), wherein the plasma concentrations of monomethyl fumarate in the subject following administration of the pharmaceutical composition in the fed state are such that the AUC (0-t) is not less than 70%, more preferably not less than 80%, most preferably not less than 90% of the AUC (0-t) achievable following administration in the fasted state.
(11) A method according to any of (1) to (10) wherein the pharmaceutical composition comprises particles of dimethyl fumarate which are not covered with a gastro-resistant coating
(12) A method according to any of (1) to (11) wherein the pharmaceutical composition comprises microcrystalline cellulose and/or croscarmellose sodium
(13) A method according to any of (1) to (12) wherein the pharmaceutical composition comprises lactose.
(14) A method according to any of (1) to (13) wherein the pharmaceutical composition comprises:
(a) particles of dimethyl fumarate;
(b) lactose;
(c) microcrystalline cellulose; and
(d) croscarmellose sodium,
(15) A method according to any one of (1) to (14), wherein the pharmaceutical composition further comprises (e) at least one glidant, preferably colloidal anhydrous silica.
(16) A method according to any one of (1) to (15), wherein the pharmaceutical composition further comprises (f) at least one lubricant, preferably magnesium stearate.
(17) A method according to any one of (1) to (16), wherein the weight ratio (c) microcrystalline cellulose to (b) lactose in the pharmaceutical composition is in the range from 2:5 to 5:2.
(18) A method according to any one of (1) to (17), wherein the pharmaceutical composition comprises, based on the total weight of the tablet before application of any coating,
(a) 20-30 wt. % of dimethyl fumarate;
(b) 25-35 wt. % of lactose;

(c) 35-45 wt. % of microcrystalline cellulose;
(d) 1-10 wt. % of croscarmellose sodium.
(19) A method according to any one of (1) to (18), wherein the pharmaceutical composition is coated with a gastro-resistant coating.
(20) A method according to (19), wherein the gastro-resistant coating comprises talc and a methacrylic acid-ethyl acetate copolymer.
(21) A pharmaceutical composition comprising:
(a) particles of dimethyl fumarate;
(b) lactose;
(c) microcrystalline cellulose; and
(d) croscarmellose sodium,
wherein the dimethyl fumarate particles are not covered with a gastro-resistant coating, for use in a method of treating the human or animal body, which method is as defined in any one of (1) to (20).
(22) Use of:
(a) particles of dimethyl fumarate;
(b) lactose;
(c) microcrystalline cellulose; and
(d) croscarmellose sodium,
wherein the dimethyl fumarate particles are not covered with a gastro-resistant coating, in the manufacture of a pharmaceutical composition, which composition is for use in a method of treating the human or animal body, which method is as defined in any one of (1) to (20).

The following Examples are given in order to provide a person skilled in the art with a sufficiently clear and complete explanation of the present invention, but should not be considered as limiting of the essential aspects of its subject, as set out in the preceding portions of this description.

EXAMPLES

Example 1

Stability (a) Bulk Composition

A 60 kg bulk composition was prepared by mixing the amounts of the ingredients detailed in Table 1.

TABLE 1

| Bulk composition | | |
|---|---|---|
| Ingredient | Weight (Kg) | % |
| Dimethyl fumarate | 15 | 25 |
| Lactose | 18 | 30 |
| Microcrystalline cellulose | 24 | 40 |
| Croscarmellose sodium | 2.4 | 4 |
| Silica colloidal anhydrous | 0.3 | 0.5 |
| Magnesium Stearate | 0.3 | 0.5 |
| Total | 60 | 100 |

Dimethyl fumarate, lactose, microcrystalline cellulose, croscarmellose sodium and silica colloidal anhydrous were mixed together to form a blend. The blend was then passed through a 0.8 mm sieve. The sieved blend was mixed again. The resulting mixture was then again passed through a 0.8 mm sieve and finally mixed again.

Magnesium stearate was passed through a 0.5 mm sieve and added to the previous blend, which was mixed to obtain the final blend.

(b) Tablets 2.1. Tablets of the Invention

The final blend of Example 1 was divided in two homothetic parts to obtain tablets with different strengths (30 and 120 mg of dimethyl fumarate). 12 Kg of bulk composition were tableted by direct compression with a rotary tableting machine to obtain 100,000 tablet cores with a final weight of 120 mg (30 mg of dimethyl fumarate) and 6.5 mm of diameter.

48 Kg of bulk composition were tableted by direct compression with a rotary tableting machine to obtain 100,000 tablet cores with a final weight of 480 mg (120 mg of dimethyl fumarate) and 11 mm of diameter.

The tablet cores were then coated with an aqueous film coating suspension comprising triethyl citrate, simethicone, talc and titanium dioxide suspended in water and methacrylic acid-ethyl acrylate copolymer (1:1) 30% aqueous dispersion (see amounts in Table 2). In the case of the 120 mg of dimethyl fumarate tablet cores, the coating suspension also contained indigo carmine lake and sodium hydroxide.

TABLE 2

| Tablets with lactose | | | |
|---|---|---|---|
| | Ingredient | 30 mg tablet weight (mg) | 120 mg tablet weight (mg) |
| Core | Dimethyl fumarate | 30 | 120 |
| | Lactose | 36 | 144 |
| | Microcrystalline cellulose | 48 | 192 |
| | Croscarmellose sodium | 4.8 | 19.2 |
| | Silica colloidal anhydrous | 0.6 | 2.4 |
| | Magnesium Stearate | 0.6 | 2.4 |
| Coating | Methacrylic acid - ethyl acrylate copolymer (1:1) 30% aqueous dispersion | 11.56 | 45.98 |
| | Talc | 5.78 | 22.94 |
| | Triethyl citrate | 1.16 | 4.61 |
| | Simethicone | 0.06 | 0.24 |
| | Titanium dioxide | 0.29 | 4.61 |
| | Indigo carmine Lake | | 1.77 |
| | 1N Sodium hydroxide solution | | 5.29 |

The enteric-coated tablets described above can be distinguished not only by the colour but also by the size (lower dose—smaller diameter; higher dose—higher diameter), which is beneficial for visually impaired people.

In addition, stability studies were conducted with the enteric-coated tablets described above following stability guidelines of the International Conference on Harmonisation of Technical Requirements for Registration of Pharmaceuticals for Human Use (ICH). Tablets were stored in a climatic chamber at 40° C./75% Relative Humidity for 6 months, 30° C./65% Relative Humidity for 12 months and at 25° C./60% Relative Humidity for 24 months. The appearance, water content, hardness, dissolution and related substances was tested at regular intervals. The results concluded that the tablets were stable. Therefore, no limitation for the storage conditions is needed.

2.2. Comparative Experiments

In a same manner as described above, 120 mg dimethyl fumarate enteric-coated tablets were prepared but replacing lactose by microcrystalline cellulose. Stability studies were conducted with this tablets at 40° C./75% Relative Humidity for 6 months in a climatic chamber. The results concluded that the tablets were not stable.

(c) Dissolution Test

The dissolution rate of dimethyl fumarate in the enteric-coated tablets of the invention described above was determined following a standard dissolution test for solid dosage forms. These dissolution tests are described in the European Pharmacopoeia 6.0, Chapter 2.9.3 and in the US Pharmacopoiea USP36-NF31, Chapter 711.

The dissolution testing was carried out as follows: A USP apparatus II (paddles) with 1 L vessels was used. Bath temperature was set to 37° C.±0.5° C. and paddle speed to 75 rpm. One tablet is placed in one vessel containing 750 mL 0.1N HCl (pH 1.2) over 2 h. After that the pH is changed to 6.2 by adding 220 mL 0.2 M sodium phosphate buffer (0.05 M phosphate buffer). The tablet is maintained under the buffered pH over 2 h. After that, samples are taken at each sampling time point (every 10 or 20 min). Dimethyl fumarate is detected by UV; cell volume 0.1 cm$^3$, detector wavelength 220 nm, reference wavelength 400-500 nm.

The pharmaceutical compositions of the invention present a dissolution profile similar to Fumaderm®, despite having reduced the number of active ingredients and having different excipients. Additionally, no relevant differences were observed among the different dissolution profiles of the pharmaceutical compositions of the invention obtained using lactose, fructose, mannitol or dibasic calcium phosphate in the tablet core.

Example 2

Non-Inferiority to Active Comparator

The safety and efficacy of a composition of the invention, Skilarence, were assessed in a double-blind, three-arm, placebo and active comparator-controlled phase III study, using patients with moderate to severe plaque psoriasis. The majority of patients reported a "very large" or "extremely large" effect of psoriasis on their life based on the Dermatology Life Quality Index (DLQI) prior to the trial commencing, with a mean DLQI score of 11.5.

Patients were randomised to receive: (i) Skilarence; (ii) an active comparator (Fumaderm); or (iii) placebo in a 2:2:1 ratio. As discussed above, Fumaderm is a combination product comprising dimethyl fumarate and three monoethyl fumarate salts.

Skilarence is a tablet coated with a gastro-resistant coating. The tablet comprises dimethyl fumarate, available in 30 mg and 120 forms. The compositions of the 30 mg and 120 mg tables are set below:

| Component | Name Skilarence gastro-resistant tablets Blister PVC/PVDC (250/90) - ALU (20) | |
|---|---|---|
| | 30 mg Quantity (mg/tablet) | 120 mg Quantity (mg/tablet) |
| Active substances | | |
| Dimethyl fumarate | 30 | 120 |
| Excipients (core) | | |
| Lactose monohydrate | 36 | 144 |
| Cellulose microcrystalline | 48 | 192 |
| Croscarmellose sodium | 4.8 | 19.2 |
| Silica colloidal anhydrous | 0.6 | 2.4 |
| Magnesium stearate | 0.6 | 2.4 |
| Excipients (coating) | | |
| Talc | 5.78 | 22.94 |
| Methacrylic acid - ethyl acrylate copolymer (1:1) | 11.56 | 45.98 |

-continued

| Component | Name Skilarence gastro-resistant tablets Blister PVC/PVDC (250/90) - ALU (20) | |
|---|---|---|
| | 30 mg Quantity (mg/tablet) | 120 mg Quantity (mg/tablet) |
| Simethicone | 0.06 | 0.24 |
| Triethyl citrate | 1.16 | 4.61 |
| Titanium dioxide (E-171) | 0.29 | 4.61 |
| Indigo carmine (E-132) | — | 1.77 |
| NaOH 1N | — | 0.24 |

Treatment started with the administration of tablets containing either 30 mg/day dimethyl fumarate or placebo. In the active treatment arms, the dose was then gradually increased as set out in Table 6:

TABLE 6

| | Dose administration | | | |
|---|---|---|---|---|
| | Number of tablets per day | | | Total daily dose |
| Week | Morning | Midday | Evening | of dimethyl fumarate |
| skilarence 30 mg | | | | |
| 1 | 0 | 0 | 1 | 30 |
| 2 | 1 | 0 | 1 | 60 |
| 3 | 1 | 1 | 1 | 90 |
| skilarence 120 mg | | | | |
| 4 | 0 | 0 | 1 | 120 |
| 5 | 1 | 0 | 1 | 240 |
| 6 | 1 | 1 | 1 | 360 |
| 7 | 1 | 1 | 2 | 480 |
| 8 | 2 | 1 | 2 | 600 |
| 9+ | 2 | 2 | 2 | 720 |

If treatment success was observed before the maximum of 720 mg/day dimethyl fumarate was reached no further increases were provided and the dose was gradually decreased to an individual maintenance dose. Treatment was continued for 16 weeks.

In the case of patient intolerability in weeks 4 to 16, the patient was returned to the last tolerated dose taken since week 4 and that dose was maintained for the rest of the treatment period of 16 weeks.

Similar dosing to that set out in Table 6 was provided in the Fumaderm treatment arm. A summary of the clinical efficacy observed in each arm of the study is set out in Table 7.

TABLE 7

Summary of clinical efficacy after 16 weeks treatment

| Assessment | Skilarence N = 267 | Placebo N = 131 | Fumaderm N = 273 |
|---|---|---|---|
| Superiority testing vs placebo | | | |
| PASI 75, n (%) | 100 (37.5) | 20 (15.3) | 110 (40.3) |
| p-value | <0.0001[a] | <0.0001[a] | |
| Two-sided 99.24% CI | 10.7, 33.7[a] | 13.5, 36.6[a] | |
| PGA score clear or almost clear, n (%) | 88 (33.0) | 17 (3.0) | 102 (37.4) |
| p-value | <0.0001[a] | <0.0001[a] | |
| Two-sided 99.24% CI | 9.0, 31.0[a] | 13.3, 35.5[a] | |

| | Skilarence N = 267 | Fumaderm N = 273 |
|---|---|---|
| Non-inferiority of Skilarence vs. Fumaderm | | |
| PASI 75, n (%) | 100 (37.5) | 110 (40.3) |
| p-value | 0.0003[b] | |
| One-sided 97.5% repeated CI (lower limit) | −11.6[b] | |
| PGA score clear or almost clear, n (%) | 88 (33.0) | 102 (37.4) |
| p-value | 0.0007[b] | |
| One-sided 97.5% repeated CI (lower limit) | −13.0[b] | | n = number of patients with available data;
N = number of patients in population;
PASI = Psoriasis Area Severity Index;
PGA = Physician's Global Assessment;
[a]Superiority of Skilarence vs. Placebo with a difference of 22.2% for PASI 75 and 20.0% for PGA score clear or almost clear, superiority of Fumaderm vs Placebo with a difference of 25.0% for PASI 75 and 24.4% for PGA score clear or almost clear;
[b]Non-inferiority of Skilarence vs. Fumaderm with a difference of −2.8% for PASI 75 and −4.4% for PGA score clear or almost clear.

The data show that, after 16 weeks, Skilarence is superior to placebo. The trend in the efficacy endpoint PASI score means % change from baseline observed indicated the onset of a clinical response to Skilarence as early as week 3 (−11.8%), and these became statistically significant compared to placebo by week 8 (−30.9%). Further improvements were seen by week 16 (−50.8%). The benefits of Skilarence were also observed from the patient self-perceived improvements in their quality of like. By 16 weeks, patients treated with Skilarence had a lower mean DLQI (5.4) compared to placebo (8.8).

After 16 weeks it was also shown that Skilarence is non-inferior to the active comparator Fumaderm based on PASI 75. The change in composition between Skilarence and Fumaderm has not, therefore, altered efficacy.

In the study described above the unfavourable effects observed are provided in Table 8.

Based on the above efficacy and safety parameters, Skilarence has been shown overall to have a comparable effect to Fumaderm.

Example 3

Improved Pharmacokinetics in the Fed State

An open-label, randomised, study comparing the pharmacokinetics of the dimethyl fumarate (DMF) metabolite, monomethyl fumarate (MMF) after a single dose of 120 mg of Skilarence (LAS41008) and Fumaderm under both the fed and fasted state was carried out. The PK results and comparative statistics are shown in Tables 9 and 10.

TABLE 9

Unfavourable Effects

| Effect | Short Description | Unit | Skilarence | Fumaderm | Placebo |
|---|---|---|---|---|---|
| Gastrointestinal effects | Diarrhoea, Abdominal pain, Nausea, Flatulence, Vomiting, Dyspepsia, Constipation | % | 60.6 | 60.1 | 27.0 |
| Skin and subcutaneous disorders | Erythema, Pruritus, Skin burning sensation | % | 21.5 | 19.4 | 8.8 |
| Vascular disorders | Flushing, hot flush | % | 21.5 | 17.0 | 2.2 |
| Blood disorders | Lymphopenia, Esoinophilia | % | 16.5 | 16.6 | 0.7 |
| Raised hepatic enzymes | ALT, GGT, AST | % | 10.8 | 8.8 | 5.8 |
| Discontinuation | Adverse events leading to treatment discontinuation | % | 24.0 | 24.4 | 5.8 |

TABLE 9

Pharmacokinetic parameters of MMF after single dose administration of 120 mg gastro-resistant tablets of Skilarence and Fumaderm in fasted and fed conditions

| Parameter | Units | Statistics | Skilarence | | Fumaderm | |
| --- | --- | --- | --- | --- | --- | --- |
| | | | Fasting | Fed | Fasting | Fed |
| $C_{max}$ | ng/mL | N | 30 | 25 | 30 | 21 |
| | | Mean ± SD | 1325 ± 537 | 1311 ± 574 | 1149 ± 637 | 1227 ± 426 |
| | | CV | 40.6 | 43.8 | 54.4 | 34.7 |
| | | Min-Max | 401-2880 | 307-2130 | 211-2550 | 380-2190 |
| $AUC_{0-t}$ | ng · h/mL | N | 30 | 24 | 30 | 29 |
| | | Mean ± SD | 1789 ± 570 | 1743 ± 533 | 1608 ± 713 | 1392 ± 860 |
| | | CV | 31.8 | 30.6 | 44.4 | 61.7 |
| | | Min-Max | 716-2966 | 668-2713 | 494-3203 | 39-2931 |

$AUC_{0-t}$: area under the plasma concentration-time curve from zero to time t, where t is the time of the last concentration measured;
$C_{max}$: maximum plasma concentration;
CV: coefficient of variation (%)

TABLE 10

Statistical analysis

| Parameter | Comparison | Ratio (%) | 90% confidential interval (%) |
| --- | --- | --- | --- |
| $C_{max}$ | Fasted: Skilarence/Fumaderm | 128.3 | 106.0-155.2 |
| | Fed: Skilarence/Fumaderm | 105.3 | 84.29-131.4 |
| | Fumaderm: fed/fasted | 116.6 | 94.01-144.5 |
| | Skilarence: fed/fasted | 95.65 | 78.10-117.1 |
| $AUC_{0-t}$ | Fasted: Skilarence/Fumaderm | 118.0 | 91.04-152.8 |
| | Fed: Skilarence/Fumaderm | 174.8* | 132.0-231.6* |
| | Fumaderm: fed/fasted | 63.89* | 49.17-83.02* |
| | Skilarence: fed/fasted | 94.71 | 71.68-125.1 |
| AUC | Fasted: Skilarence/Fumaderm | 117.8 | 105.6-131.5 |
| | Fed: Skilarence/Fumaderm | 92.54 | 80.63-106.2 |
| | Fumaderm: fed/fasted | 122.9 | 107.7-140.3 |
| | Skilarence: fed/fasted | 96.52 | 85.54-108.9 |

*Statistical analysis performed using all evaluable $AUC_{0-t}$ values according to the criteria previously described. However, 10 subjects showed ascending PK profiles at 24 h and, therefore, the $AUC_{0-t}$ values used in the analysis may be considered as truncated AUCs rather than true $AUC_{0-t}$ values.

As can also be seen from the data above, the ratio of $AUC_{(0-t)}$ Skilarence/Fumaderm is higher in the fed state than for the fasted state, whereas the $C_{max}$ Skilarence/Fumaderm is higher in the fasted state than the fed state.

The invention claimed is:

1. A method of treating an inflammatory or autoimmune disease or disorder in a subject, which method comprises orally administering to the subject a therapeutically effective amount of a pharmaceutical composition in the form of a tablet comprising:
   (a) 30 mg, 120 mg or 240 mg of particles of dimethyl fumarate;
   (b) lactose;
   (c) microcrystalline cellulose; and
   (d) croscarmellose sodium,
   wherein the pharmaceutical composition comprises, based on the total weight of the tablet before application of any coating,
      20-30 wt. % of dimethyl fumarate;
      25-35 wt. % of lactose;
      35-45 wt. % of microcrystalline cellulose;
      1-10 wt. % of croscarmellose sodium, and
   wherein the dimethyl fumarate particles are not covered with a gastro-resistant coating, wherein the composition is administered to the subject during or within 1 hour after a meal,
   and wherein the plasma concentrations of monomethyl fumarate in the subject following administration of the pharmaceutical composition are such that the AUC (0-t) is from 12.5 to 16.5 ng·h/mL per mg of the dimethyl fumarate in the pharmaceutical composition, wherein t is the time of the last concentration measured.

2. A method according to claim 1, wherein the pharmaceutical composition further comprises (e) at least one glidant.

3. A method according to claim 2, wherein the glidant (e) is colloidal anhydrous silica.

4. A method according to claim 1, wherein the pharmaceutical composition further comprises (f) at least one lubricant.

5. A method according to claim 4, wherein the lubricant is magnesium stearate.

6. A method according to claim 1, wherein the weight ratio (c) microcrystalline cellulose to (b) lactose in the pharmaceutical composition is in the range from 2:5 to 5:2.

7. A method according to claim 1, wherein the pharmaceutical composition is coated with a gastro-resistant coating.

8. A method according to claim 7, wherein the gastro-resistant coating comprises talc and a methacrylic acid-ethyl acetate copolymer.

9. A method according to claim 1, wherein the pharmaceutical composition is administered during or immediately after a meal.

10. A method according to claim 1, wherein the inflammatory or autoimmune disease or disorder is selected from rheumatoid arthritis, multiple sclerosis (MS), amyotrophic lateral sclerosis, Crohn's disease, ulcerative colitis, systemic lupus erythematosus (SLE), myastenia gravis, acute disseminated encephalomyelitis, idiopathic thrombocytopenic purpura, Sjoegren's syndrome, autoimmune hemolytic anemia (AIHA), type I diabetes or psoriasis.

11. A method according to claim 10, wherein the inflammatory or autoimmune disease or disorder is psoriasis.

12. A method according to claim 1, wherein the plasma concentrations of monomethyl fumarate in the subject following administration of the pharmaceutical composition are such that the Cmax is less than 120% of that achievable by administration of a corresponding Fumaderm formulation having the same amount of dimethylfumarate, and the AUC (0-t) is greater than 130% of that achievable by administration of a corresponding Fumaderm formulation having the same amount of dimethylfumarate,
  wherein the Fumaderm formulation is a tablet which contains dimethylfumarate, calcium monoethylfumarate, magnesium monoethylhydrogenfumarate, zinc monoethylfumarate, and croscarmellose sodium, magnesium stearate, microcrystalline cellulose, and colloidal anhydrous silica, wherein the tablet is coated with a enteric coating which contains talc and methacrylic acid-methyl methacylate copolymer (1:1), and wherein the enteric coating may also contain Macrogol 6000, simethicone, povidone, triethyl citrate, titanium dioxide and indigo carmine (E-132).

13. A method according to claim 1, wherein the subject is a human.

14. A method according to claim 1, wherein the subject is an animal.

15. A method according to claim 1, wherein the plasma concentrations of monomethyl fumarate in the subject following administration of the pharmaceutical composition are such that the AUC (0-t) is from 13 to 15 ng·h/mL per mg of the dimethyl fumarate in the pharmaceutical composition.

16. A method according to claim 12, wherein the plasma concentrations of monomethyl fumarate in the subject following administration of the pharmaceutical composition are such that the Cmax is less than 110% of that achievable by administration of a corresponding Fumaderm formulation having the same amount of dimethylfumarate, and the AUC (0-t) is greater than 150% of that achievable by administration of a corresponding Fumaderm formulation having the same amount of dimethylfumarate.

* * * * *